United States Patent
Chang et al.

(10) Patent No.: US 8,084,043 B2
(45) Date of Patent: Dec. 27, 2011

(54) **SUBUNIT VACCINE OF *PASTEURELLA MULTOCIDA* IN VETERINARY USES**

(75) Inventors: Poa-Chun Chang, Taichung (TW); Jin-Ru Wu, Taichung (TW); Jui-Hung Shien, Taichung (TW); Happy K. Shieh, Taichung (TW)

(73) Assignee: National Chung-Hseng University, Taichung (TW)

( * ) Notice: Subject to any disclaimer, the term of this patent is extended or adjusted under 35 U.S.C. 154(b) by 401 days.

(21) Appl. No.: 12/073,306

(22) Filed: Mar. 4, 2008

(65) Prior Publication Data

US 2009/0246229 A1  Oct. 1, 2009

(30) Foreign Application Priority Data

Mar. 9, 2007  (TW) ............................... 96108321 A (51) Int. Cl.
*A61K 39/102* (2006.01)
*A61K 39/00* (2006.01)
*A61K 39/02* (2006.01)
*A61K 38/00* (2006.01)

(52) U.S. Cl. ............... 424/255.1; 424/184.1; 424/234.1; 530/300

(58) Field of Classification Search .................. None
See application file for complete search history.

(56) References Cited

FOREIGN PATENT DOCUMENTS

EP  1 350 796 A1 * 10/2003

OTHER PUBLICATIONS

Wu et al (Vaccine 25, 2007, p. 4140-4148, Available online Mar. 20, 2007).*

* cited by examiner

*Primary Examiner* — Vanessa L. Ford
(74) *Attorney, Agent, or Firm* — Pai Patent & Trademark Law Firm; Chao-Chang David Pai (57) ABSTRACT

The present invention declaims the use of *Pasteurella* lipoprotein E (PlpE) as a subunit vaccine and the use of vaccines containing PlpE to protect animals from diseases caused by *P. multocida*. The results of vaccination and challenge experiments showed that mice and chickens immunized with PlpE were completely protected animals from challenge infection with $10^1$-$10^3$ $LD_{50}$ of *P. multocida* and no adverse effect was observed.

SUBUNIT VACCINE OF *PASTEURELLA MULTOCIDA* IN VETERINARY USES

FIELD OF THE INVENTION

The present invention relates to the use of *Pasteurella* lipoprotein E (PlpE) in a subunit vaccine, and the use of vaccines containing PlpE to protect animals from diseases caused by *P. multocida*.

BACKGROUND OF THE INVENTION

*Pasterurella multocida* is classified into family Pasteurellaceae, genus *Pasteurella*, and multocida means "causing many kinds of animal disease" in Latin. In the past, the taxonomic situation of Pasteurellaceae was ambiguous and arguable. However, according to the sequence analysis of 16s-RNA, Pasteurellaceae is classified into a gamma sub-group of purple bacteria, which is Gram-negative facultative anaerobe, and homologous to *Enterobacteriaaceae*. *Pasteurella multocida* is an important pathogen of domestic animals and an opportunistic pathogen of humans. Human infections with *P. multocida* largely arise from the bite of an infected carnivore, but other types of infections are occasionally reported (Hubbert W T, et al., Am J Public Health 1970; 60:1109-17). *P. multocida* has wide host range, and is the causative agent of fowl cholera in domestic birds, haemorrhagic septicaemia in cattle or sheep, and atrophic rhinitis in pigs (Hunt M L, et al., Vet Microbiol 2000, 72:3-25). Most *P. multocida* strains are highly pathogenic to murine and rabbits, which can result in acute septic symptoms at an infection dose of 1-10 CFU.

In domestic birds, *P. multocida* causes acute septic disorders in turkey, chicken, duck, and goose, which may lead to a great loss in economy. Of the five capsular serotypes (A, B, D, E and F) and 16 LPS serotypes, fowl cholera is mainly caused by serotypes A:1, A:3 and A:4 (Glisson J R. In: Saif Y M, editor. Diseases of poultry. Iowa State University Press, Ames, Iowa, 2003:657-90). Although both live-attenuated vaccines and bacterins are available, outbreaks of fowl cholera continue to occur. Live-attenuated vaccines have the disadvantage of reversion to virulence, while bacterins do not protect hosts against heterologous challenge (Bierer B W, Derieux W T, Poult Sci 1972; 51:408-16; and Rebers P A, Heddleston K L, Avian Dis 1977; 21:50-56). These disadvantages call for the development of a new type of vaccine for *P. multocida*.

In a previous report, a lipoprotein, designated *Pasteurella* lipoprotein E (PlpE), from *Mannheimia haemolytica* (formerly known as *Pasteurella haemolytica*), was found to be highly immunogenic in cattle (Confer A W, et al., Vaccine 2003; 21:2821-9). PlpE is a lipid-modified, surface-exposed outer membrane protein that is important in complement-mediated killing of *M. haemolytica* (Pandher K, et al., Infect Immun 1998; 66:5613-9). Addition of recombinant PlpE to the commercial *M. haemolytica* vaccine markedly enhanced the vaccine-induced resistance against experimental challenge with serotypes 1 and 6. A bioinformatics-based sequence search showed that a gene annotated PlpE is present in the published genome sequence of *P. multocida* strain pm-70 (serotype A:3) (May B J, et al., Proc Natl Acad Sci USA 2001; 98:3460-5). This gene has the potential to encode a lipoprotein of 335 amino acids that has 24.3% sequence identity with PlpE of *M. haemolytica* and 19.1% identity with OmlA of *A. pleuropneumoniae*. It has not yet been determined whether the PlpE of *P. multocida* could serve as a vaccine antigen by using mice and/or chicken as animal models.

Therefore, the present invention first finds out a new use of *Pasteurella* lipoprotein E (PlpE) in controlling infective diseases caused by *P. multocida*, or related disorders thereof, and further develops a subunit vaccine for protecting animal from diseases caused by *P. multocida*. The subunit vaccine of present invention is characterized by using recombinant PlpE protein as active antigen, which has no adverse side effect of forming fibrosarcoma. Additionally, the present subunit vaccine of *P. multocida* can provide a predominant protective effect against the challenge of homologous and/or heterologous serotypes in immunized animals over traditional inactivated or live-attenuated vaccines.

SUMMARY OF THE INVENTION

In one aspect, the present invention provides a subunit vaccine for protecting animal from diseases caused by *P. multocida*, which is characterized by comprising *Pasteurella* lipoprotein E (PlpE) as antigen, and a veterinary acceptable adjuvant. In one embodiment, the *Pasteurella lipoprotein E* is a protein having the amino acid sequence as listed in SEQ ID EF219452-EF219457 (SEQ ID NO:2, 4, 6, 8, 10 and 12), or an amino acid sequence with similarity of more than 90% to the amino acid sequence as listed in SEQ ID EF219452-EF219457 (SEQ ID NO:2, 4, 6, 8, 10 and 12). In another embodiment, the disease caused by *P. multocida* is fowl cholera in domestic birds, haemorrhagic septicaemia in cattle, or atrophic rhinitis in pigs.

In another aspect, the present invention provides a use of *Pasteurella* lipoprotein E in controlling infective diseases caused by *P. multocida*, or related disorders thereof. The disease caused by *P. multocida* infection may be fowl cholera in domestic birds, haemorrhagic septicaemia in cattle, or atrophic rhinitis in pigs. In other animals, such as mice, rabbits, cats, or dogs, *P. multocida* infection may cause haemorrhagic septicaemia.

DETAILED DESCRIPTION OF THE INVENTION

The present invention will be further defined by reference to the following examples, which are set forth to assist in understanding the invention and should not be construed as specifically limiting the invention. Therefore, any modification or derivative made without departing from the spirit of this invention will be considered to fall within the scope of the invention.

EXAMPLE

Example 1

Preparation of Recombinant Lipoprotein E (r-PlpE) of *P. multocida* in *E. coli*

A. Bacterial Strains and Genomic DNA Extraction of *P. multocida*

*P. multocida* standard strains X-73 (A:1), P-1059 (ATCC 15742) (A:3), and P-1662 (A:4) were grown at 37° C. in BRAIN-HEART INFUSION (BHI) broth (Difco Laboratories, MI, USA) for 18-24 hours. Bacterial genomic DNA was isolated using the DNEASY® TISSUE KIT (QIAGEN, Hilden, Germany).

B. Genetic Cloning and Expression Vector Construction for Recombinant Lipoprotein E (r-PlpE)

One set of primers, P1 and P2, was used to amplify the PlpE gene from *P. multocida* strain X-73. The amplified genes were then used for expressing recombinant PlpE (r-PlpE) in *E. coli*. These primers contained restriction enzyme (NcoI or XhoI) cutting sites at their 5'-ends (underlined sequences), followed by sequences specific to PlpE. The PCR product was cloned into the expression vector pET28a according to the manufacturer's instructions (Novagen, Inc. Madison, Wis.) to obtain a plasmid designated as pX73-PlpE. The identity of the insert in pET28a was verified by DNA sequence analysis. The amino sequence of r-PlpE protein is described in SEQ ID: 2.

C. Expression and Purification of Recombinant Lipoprotein E (r-PlpE)

Recombinant plasmid pX73-PlpE obtained in section B was transformed into *E. coli* strain BL21 (DE3) and recombinant protein was purified by nickel chromatography as previously described (Chang P C, et al., 2002, Avian Dis 46:570-80). In brief, *E. coli* strain BL21 (DE3) harboring the recombinant plasmid was cultured in LB medium at 37° C. until absorbance at 600 nm reached 0.6. Isopropylthio-β-D-thiogalactose (IPTG) was added to a final concentration of 0.4 mM, and the culture was grown for another 3 hrs. Cells were pelleted by centrifugation at 3000×g for 20 min, and resuspended in 2 ml of binding buffer (20 mM pH 7.9 Tris, 5 mM imidazole, 500 mM NaCl). The suspension was sonicated and centrifuged at 12,000×g for 40 min. The supernatant was collected and loaded into a column containing 2.5 ml of "His-bind" resin (Novagen). The column was washed with 25 ml of binding buffer and 15 ml of washing buffer (20 mM pH 7.9 Tris, 50 mM imidazole, 500 mM NaCl) to remove the unbound proteins. The bound protein was eluted with 15 ml of eluting buffer (20 mM pH 7.9 Tris, 250 mM imidazole, 500 mM NaCl), only the first 3 ml of the elute was collected. Protein concentration was determined using a "Protein Assay" kit (BIO-RAD, Hercules, Calif., USA).

The expression product and purity of the recombinant protein was observed by SDS-PAGE and Western blotting analysis, respectively. The results were showed in FIG. 1. The r-PlpB in FIG. 1 was a noneffective subunit vaccine used as a control in the experiments. The plpB and plpE genes were cloned from *P. multocida* strain X-73 (serotype A:1) and then expressed in *E. coli* as recombinant proteins. The recombinant PlpB (r-PlpB) and PlpE (r-PlpE) contained a hexa-histidine-tag attached at their carboxyl termini.

As showed in FIG. 1, the calculated molecular masses of r-PlpB and r-PlpE were 31.5 and 38.7 kDa, respectively. Both r-PlpB and r-PlpE contained a signal peptide of 20 amino acid residues at their amino termini, and after cleavage of the signal peptide, the matured r-PlpB and r-PlpE had molecular masses of 29.3 and 36.3 kDa, respectively. As shown in FIG.

1A, r-PlpB and r-PlpE, with the expected molecular masses, were highly expressed in *E. coli* and were purified using nickel chromatography (FIG. 1A).

Western blot analyses using anti-hexa-histidine monoclonal antibody showed that this monoclonal antibody reacted with r-PlpB and r-PlpE (FIG. 1B); moreover, both r-PlpB and r-PlpE produced two bands on the blot, the major band having the molecular mass corresponding to the full-length r-PlpB or PlpE (31.5 or 38.7 kDa), whereas the minor band had the molecular mass of the mature form (29.3 or 36.3 kDa) (FIG. 1B). This result suggests that some processing of r-PlpB and r-PlpE occurred in *E. coli*. The bands corresponding to r-PlpB, r-PlpE and their processed products are indicated by arrows.

Example 2

Evaluation of Protective Effects of r-PlpE Subunit Vaccine in BALB/c Mice Model Three experiments were conducted in BALB/c mice. In experiments 1 and 2, groups of 6-week-old mice were immunized subcutaneously with 10 micrograms of purified r-PlpB or r-PlpE in aluminum hydroxide adjuvant (Sigma-Aldrich Co., MO, USA), either alone or together with a bacterin composed of $1.25\times10^7$ or $2.5\times10^7$ CFU of formalin-inactivated *P. multocida* X-73 (A:1). Two weeks after immunization, mice were challenged with subcutaneous injection of 10-20 $LD_{50}$ of strain X-73. In experiment 3, mice were immunized as described for experiments 1 and 2. Two weeks after immunization, mice were challenged with subcutaneous injection of 10 $LD_{50}$ of strains P-1059 (A:3) or P-1662 (A:4), or strain T2A5 (which is a designated challenge strain used in drug inspection in Taiwan). All mice challenged were observed for 10 days and their survival rates were recorded. The results are summarized in Table 1. For statistical analysis, the survival rates were compared by Chi-squared tests using SAS® software (SAS Institute, Inc., Cary, N.C., USA). The mean times to death were compared using the GLM procedure in the same software. Differences were considered significant when $p<0.05$.

TABLE 1

Results of immunization and challenge tests in BALB/c mice.

| Immunized with[1] | Challenge strain and dose[2] | % survival[3] |
|---|---|---|
| Exp. 1 | X-73 (A:1) | |
| Control | 30 CFU | 0 (0/6)[a] |
| r-PlpB (10 microgram) | 30 CFU | 0 (0/10)[a] |
| r-PlpE (10 microgram) | 30 CFU | 100 (10/10)[b] |
| Inactivated X-73 ($2.0 \times 10^8$ CFU) | 30 CFU | 100 (6/6)[b] |
| Inactivated X-73 ($1.25 \times 10^7$ CFU) | 30 CFU | 17 (1/6)[a] |
| Inactivated X-73 ($1.25 \times 10^7$ CFU) + r-PlpB (10 microgram) | 30 CFU | 30 (3/10)[a] |
| Inactivated X-73 ($1.25 \times 10^7$ CFU) + r-PlpE (10 microgram) | 30 CFU | 10 (10/10)[b] |
| Exp. 2 | X-73 (A:1) | |
| Control | 60 CFU | 0 (0/6)[a] |
| r-PlpB (10 microgram) | 60 CFU | 10 (1/10)[a] |
| r-PlpE (10 microgram) | 60 CFU | 80 (8/10)[bc] |
| Inactivated X-73 ($2.5 \times 10^7$ CFU) | 60 CFU | 50 (3/6)[ab] |
| Inactivated X-73 ($2.5 \times 10^7$ CFU) + r-PlpB (10 microgram) | 60 CFU | 40 (4/10)[ab] |
| Inactivated X-73 ($2.5 \times 10^7$ CFU) + r-PlpE (10 microgram) | 60 CFU | 90 (9/10)[c] |
| Exp. 3 | P-1059 (A:3) | |
| Control | 35 CFU | 0 (0/5)[a] |

TABLE 1-continued

Results of immunization and challenge tests in BALB/c mice.

| Immunized with[1] | Challenge strain and dose[2] | % survival[3] |
|---|---|---|
| r-PlpE (10 microgram) | 35 CFU P-1662 (A:4) | 100 (10/10)[b] |
| Control | 30 CFU | 0 (0/5)[a] |
| r-PlpE (10 microgram) | 30 CFU T2A5 (A:1) | 100 (10/10)[b] |
| Control | 3 CFU | 0 (0/5)[a] |
| r-PlpE (10 microgram) | 3 CFU | 80 (8/10)[b] |

[1]Mice in the control group were not immunized.
[2]The $LD_{50}$ of strains X-73 and P1662 in mice was <3 CFU, and that of P-1059 was 3.5 CFU.
[3]Different alphabetical characters indicate significant difference (p < 0.05) between groups.

In experiment 1, mice immunized with 10 microgram of purified r-PlpE were completely protected (100% survival) (Table 1, experiment 1). In contrast, mice immunized with 10 microgram of purified r-PlpB were not protected (0% survival) against challenge infection with 30 CFU (>10 $LD_{50}$) of X-73 (serotype A:1). Mice immunized with a bacterin composed of $2 \times 10^8$ CFU of formalin-inactivated X-73 were completely protected (100% survival), whereas those immunized with a bacterin composed of a lower dose ($1.25 \times 10^7$ CFU) of X-73 were not protected (17% survival) (Table 1, experiment 1). To investigate whether r-PlpB or r-PlpE could enhance the protective efficacy of the bacterin, mice were immunized with a bacterin composed of $1.25 \times 10^7$ CFU of X-73 supplemented with 10 microgram r-PlpB or r-PlpE. The results showed that r-PlpB did not significantly enhance the protective efficacy of the bacterin (30% survival, p>0.05) whereas r-PlpE did (100% survival, p<0.05) (Table 1, experiment 1).

In experiment 2, the challenge dose of X-73 was increased to 60 CFU (>20 $LD_{50}$) and a bacterin composed of $2.5 \times 10^7$ CFU of X-73 was used. The results showed that mice immunized with 10 microgram of r-PlpB were not protected (10% survival) whereas those with 10 microgram of r-PlpE were significantly protected (80% survival, p<0.05) (Table 1, experiment 2). Mice immunized with a bacterin composed of $2.5 \times 10^7$ CFU of X-73 were moderately protected (50% survival). Mice immunized with the same bacterin supplemented with r-PlpB showed a survival rate of 40%, which was similar to that with the bacterin alone. In contrast, mice immunized with the bacterin supplemented with r-PlpE showed a survival rate of 90%, which was significantly higher than that with the bacterin alone (p<0.05) (Table 1, experiment 2).

In experiment 3, strains P-1059 (serotype A:3) and P-1662 (serotype A:4) were used as the challenge strains. The results showed that mice immunized with 10 microgram of r-PlpE were completely protected against challenge infection with 10 $LD_{50}$ of P-1059 or >10 $LD_{50}$ of P-1662 (Table 1, experiment 3). This result showed that r-PlpE, which was derived from X-73 (serotype A:1), conferred cross protection on mice against challenge with strains of serotypes A:3 and A:4. Additionally, mice immunized with 10 microgram of r-PlpE showed a survival rate of 90% when challenge with strain T2A5 (A:1), which was up to the proof inspection standard (survival rate of 60%) (p<0.05) (Table 1, experiment 3).

Example 3

Evaluation of Protective Effects of r-PlpE Subunit Vaccine in SPF Chicken Model

Three experiments in SPF chickens were conducted. In experiment 1, groups of 3-week-old SPF chickens were immunized subcutaneously with 100 micrograms of purified r-PlpB or r-PlpE in complete Freund's adjuvant (Sigma-Aldrich). Three weeks after the primary immunization, a booster immunization was conducted, and three weeks after booster immunization, chickens were challenged with intramuscular injection of $3.6\times10^3$ CFU of strain X-73 or $5.5\times10^8$ CFU of strain P-1662. In experiments 2 and 3, chickens were immunized subcutaneously twice with 125 micrograms of a crude extract of r-PlpE in a double emulsion adjuvant with a 3-week interval between immunizations. The crude extract was prepared by sonicating the pellet of *E. coli* that expressed r-PlpE. The double emulsion adjuvant contained Marcol 52 oil (63%), Arlacel A (7%), and Tween 80 (1.5%). Three weeks after booster immunization, chickens were challenged by intramuscular injection of $3.6\times10^3$–$3.6\times10^6$ CFU of strain X-73 or $5.5\times10^7$–$5.5\times10^9$ CFU of strain P-1662. All chickens challenged were monitored for 10 days and the survival rates were recorded. The results are summarized in Table 2. For statistical analysis, the survival rates were compared by Chi-squared tests using SAS® software (SAS Institute Inc., Cary, N.C., USA). The mean times to death were compared using the GLM procedure in the same software. Differences were considered significant when p<0.05.

TABLE 2

Results of immunization and challenge tests in SPF chickens

| Immunized with [1] | Challenge strain and dose [2] | % survival [3] | Mean time to death (days) [3] |
|---|---|---|---|
| Exp. 1 | X-73 (A:1) | | |
| Control | $3.6 \times 10^3$ CFU | 30 (3/10)[a] | 3.3[a] |
| Purified r-PlpB (100 microgram) | $3.6 \times 10^3$ CFU | 50 (5/10)[a] | 4.2[a] |
| Purified r-PlpE (100 microgram) | $3.6 \times 10^3$ CFU | 100 (10/10)[b] | NA |
| | P-1662 (A:4) | | |
| Control | $5.5 \times 10^8$ CFU | 13 (1/8)[a] | 4.1[a] |
| Purified r-PlpB (100 microgram) | $5.5 \times 10^8$ CFU | 13 (1/8)[a] | 5.4[a] |
| Purified r-PlpE (100 microgram) | $5.5 \times 10^8$ CFU | 63 (5/8)[b] | 5.7[a] |
| Exp. 2 | X-73 (A:1) | | |
| Control | $3.6 \times 10^3$ CFU | 25 (2/8)[a] | 2.7[a] |
| | $3.6 \times 10^4$ CFU | 0 (0/8)[a] | 1.9[a] |
| | $3.6 \times 10^5$ CFU | 0 (0/8)[a] | 2.0[a] |
| Crude extract r-PlpE | $3.6 \times 10^3$ CFU | 100 (8/8)[b] | NA |
| (125 microgram) | $3.6 \times 10^4$ CFU | 75 (6/8)[b] | 7.0[b] |
| | $3.6 \times 10^5$ CFU | 75 (6/8)[b] | 5.0[b] |
| | $3.6 \times 10^6$ CFU | 88 (7/8)[b] | 4.0[b] |

TABLE 2-continued

Results of immunization and challenge tests in SPF chickens

| Immunized with [1] | Challenge strain and dose [2] | % survival [3] | Mean time to death (days) [3] |
|---|---|---|---|
| Exp. 3 | P-1662 (A:4) | | |
| Control | $5.5 \times 10^7$ CFU | 25 (2/8)[a] | 5.7[a] |
| | $5.5 \times 10^8$ CFU | 13 (1/8)[a] | 4.1[a] |
| | $5.5 \times 10^9$ CFU | 0 (0/8)[b] | 2.9[a] |
| Crude extract r-PlpE | $5.5 \times 10^7$ CFU | 50 (4/8)[a] | 4.8[a] |
| (125 microgram) | $5.5 \times 10^8$ CFU | 50 (4/8)[a] | 4.8[a] |
| | $5.5 \times 10^9$ CFU | 50 (4/8)[a] | 5.3[a] |

[1] Immunization was conducted twice with a 3-week interval. Chickens in the control group were not immunized.
[2, 3] Different alphabetical characters indicate significant difference (p < 0.05) between immunization and control groups challenged with the same dose of X-73 or P-1662.

In experiment 1, chickens immunized twice with 100 microgram of purified r-PlpB showed a survival rate of 50% against challenge with X-73, but this survival rate was not significantly higher than that of the control group (30% survival, p>0.05). In contrast, chickens immunized twice with 100 microgram of purified r-PlpE showed a survival rate of 100%, which was significantly higher than that of the control group (p<0.05) (Table 2. experiment 1). This result suggests that r-PlpE but not r-PlpB conferred protection on chickens. A similar conclusion was reached when strain P-1662 was used as the challenge strain (Table 2, experiment 1).

Figure 1:
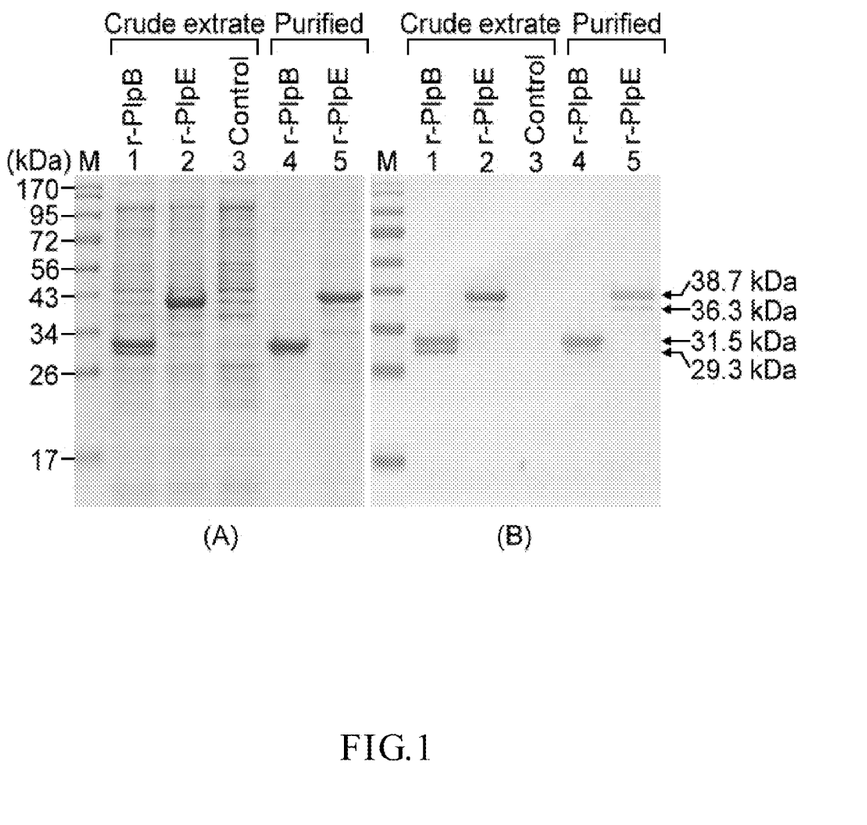
FIG. 1. Expression and purification of recombinant PlpE (r-PlpE) and recombinant PlpB (r-PlpB) in *E. coli*. Note that r-PlpB was used as the control antigen in this report. (A) Coomassie blue-stained SDS-PAGE of recombinant proteins from crude extract or purified samples. Lane M represents the molecular mass markers. The lanes marked control contain crude extract of *E. coli* that harbored no recombinant plasmid. (B) Immunoblot of duplicated gel probed with mouse anti-hexa-histidine monoclonal antibody. The bands corresponding to r-PlpB, r-PlpE, and their processed products are indicated by arrows.

In experiments 2 and 3, a crude extract of r-PlpB and r-PlpE (FIG. 1A), instead of the purified one, was used as the antigen. Moreover, a double emulsion adjuvant, instead of Freund's complete adjuvant, was used as the emulsifying agent. These modifications were carried out to reduce the cost and labor required for preparation and administration of the antigen. The results showed that chickens immunized twice with 125 microgram of crude extract of r-PlpE had a survival rate of 75-100% against challenge with $3.6 \times 10^3$–$3.6 \times 10^6$ CFU of strain X-73. These rates were significantly higher than those of the control group (p<0.05) (Table 2, experiment 2). Moreover, the mean time to death of chickens immunized with r-PlpE was significantly longer than that of the control group (p<0.05) (Table 2, experiment 2).

In experiment 3, P-1662 was used as the challenge strain. The results showed that chickens immunized with 125 microgram of crude extract of r-PlpE had a survival rate of 50% against challenge with $5.5 \times 10^7$–$5.5 \times 10^9$ CFU of strain P-1662. These rates were not significantly higher than those of the control groups (p>0.05), except when the challenge dose of P-1662 was $5.5 \times 10^9$ (p<0.05) (Table 2, experiment 3). The mean times to death of immunized chickens were not significantly longer than those of the control groups (p>0.05) (Table 2, experiment 3).

Example 4

Nucleotide Sequences of plpE from Reference Strains of *P. multocida*

Two primers, P3 and P4, were used to amplify the PlpE genes from different reference strains of *P. multocida*, X-73 (A:1), pm-70 (A:3), P-470 (A:3), P-61 (D:3), P-1059 (A:3), P-1662 (A:4), and ATCC 12948 (D:11). The two primers were designed on the basis of the published genome sequence of *P. multocida* strain pm-70. P3 and P4 amplified the 1.0 kb DNA fragment containing the PlpE gene. The sequences of primers P3 and P4 were as follows. P3: 5'-ATG AAA CAA ATC GTT TTA AA-3' (SEQ ID NO:13), and P4: 5'-TTA TTG TGC TTG GTG ACT TT-3' (SEQ ID NO:14). The PCR products were purified with a QIAQUICK® GEL EXTRACTION KIT (QIAGEN) and sequenced from both directions using a BIGDYE® TERMINATOR CYCLE SEQUENCING KIT (Applied Biosystems, Foster City, Calif.) in an automatic sequencer (ABI-3730XL DNA ANALYZER®, Applied Biosystems). Sequences were compiled using the SEQMAN® program in the LASERGENE® package (DNASTAR Inc. Madison, Wis., USA). Open reading frames prediction and antigenic index assay were performed using the GENEQUEST and PROTEAN programs from the same package. Nucleotide and protein sequences were searched for homology in GenBank using the BLAST program provided by NCBI, USA.

The nucleotide sequences of the PlpE gene determined in this study are available in GenBank under the accession numbers EF219452-EF219457 (corresponding to the SEQ ID NO:1, 3, 5, 7, 9, and 11) in the appending sequence listing). All these PlpE genes were found to contain an open reading frame of 1008-1019 nt, encoding a PlpE protein of 37.4-37.7 kDa. Pair-wise sequence comparison showed that these PlpE proteins had 90.8-100% sequence identity with each other, suggesting that PlpE might serve as a cross-protective antigen. This is the first report of a recombinant *P. multocida* antigen that confers cross protection on animals. Therefore, a protein having the amino acid sequence as listed in SEQ ID NO:2, 4, 6, 8, 10, and 12, or an amino acid sequence with similarity of more than 90% to the amino acid sequence as listed in SEQ ID NO:2, 4, 6, 8, 10, and 12, is considered to exhibit highly similar protective effects, and contemplates to be included in the subunit vaccine of the present invention.

The above examples are given by way of illustration only, and should not be construed as specifically limiting the scope of present invention. Any variation of the invention described and claimed herein, including the substitution of all equivalents, which would be within the purview of those skilled in the art, is to be considered to fall within the scope of the invention incorporated herein.

The strain *E. coli* BL21 (DE3) containing the recombinant vector X73-plpE of the invention was deposited with the Agricultural Research Service Culture Collection (NARRL), on Feb. 29, 2008, as Deposit No. NARRL B-50117.

The invention claimed is:

1. A subunit vaccine composition for controlling animal diseases caused by *P. multocida*, the subunit vaccine composition comprising recombinant *Pasteurella* lipoprotein E (PlpE) as an antigen, and a veterinary acceptable adjuvant, wherein the *Pasteurella* lipoprotein E is a protein having the amino acid sequence identified by SEQ ID NO:2.

2. A subunit vaccine composition of claim 1, wherein the animal disease caused by *P. multocida* is haemorrhagic septicaemia and pneumonic pasteurellosis in cattle.

3. A subunit vaccine composition of claim 1, wherein the animal disease caused by *P. multocida* is fowl cholera.

4. A subunit vaccine composition of claim 1, wherein the animal disease caused by *P. multocida* is atrophic rhinitis and pneumonic pasteurellosis in pigs.

* * * * *

SEQUENCE LISTING

<160> NUMBER OF SEQ ID NOS: 14

<210> SEQ ID NO 1
<211> LENGTH: 1011
<212> TYPE: DNA
<213> ORGANISM: P. multocida strain X-73
<300> PUBLICATION INFORMATION:
<308> DATABASE ACCESSION NUMBER: EF219452
<309> DATABASE ENTRY DATE: 2007-05-17

<400> SEQUENCE: 1

| | | | | | |
|---|---|---|---|---|---|
| atgaaacaaa | tcgttttaaa | aacaagctta | ttgatgaccc | tctcttcatt | attagtggca | 60 |
| tgtagcggtg | gtggcggtag | cgctggaaat | cgtgctgacc | gtgtagagga | aaaagcacaa | 120 |
| ccggttcaat | caaatagtga | gccttcttcc | actccaatca | acatcctat | gactaatagt | 180 |
| gctacgaata | cttctcttca | tgacaaactt | tcaatgtctt | ctcatgacac | atccaaagaa | 240 |
| aatagtcaac | aatcctccct | tcaagcccct | ctagaacaag | aaaaaaacca | acctgcacaa | 300 |
| gaaaatctta | cttggacagg | ttatcatgtt | tcagaatggg | gaaatgcgag | taataatgta | 360 |
| gataaagata | atgttacggt | attcactttc | gtaaaatata | attctcaata | taatgatgat | 420 |
| ccagttttg | ataaaacaaa | aacacaaagt | aaaacgatat | cattagttga | cggaaaaaat | 480 |
| gaaaataaag | agcattatta | tcactttacg | ctaaagacg | attattttta | ttatggcagt | 540 |
| tatggacaac | cttcatcaga | ttataaaaaa | atagaagaaa | actatattta | tgcaatcaaa | 600 |
| ccagatgcaa | taataatga | aacatcaat | gcactaactg | caacttacca | tcaagaagat | 660 |
| ggttttatat | attccgtatt | aagtgatgta | aatcgagttg | gttcagaata | tattcctcag | 720 |
| tatggcaatg | tgagtcttac | tatacaaaat | ggtaaaattt | atggtgagat | ttataggcat | 780 |
| aaccgagggt | acgatgatct | atttaagctc | tctggagaag | gtcggaattt | aatattaaca | 840 |
| ccacataaaa | ataaccctta | tgatctttcc | cctacaggac | ccgacaacat | gacaatggag | 900 |
| ctgaatttta | tcaacgcaga | aaagactgat | aaaaaatacg | ttgttggtgt | aggaaaagct | 960 |
| gaaaaatatt | atgggttatt | atttgctgaa | aaaagtcacc | aagcacaata | a | 1011 |

<210

Asp Lys Asp Asn Val Thr Val Phe Thr Phe Val Lys Tyr Asn Ser
            125                 130                 135

Gln Tyr Asn Asp Asp Pro Val Phe Asp Lys Thr Lys Thr Gln Ser
            140                 145                 150

Lys Thr Ile Ser Leu Val Asp Gly Lys Asn Glu Asn Lys Glu His
            155                 160                 165

Tyr Tyr His Phe Thr Leu Lys Asp Asp Leu Phe Tyr Tyr Gly Ser
            170                 175                 180

Tyr Gly Gln Pro Ser Ser Asp Tyr Lys Lys Ile Glu Glu Asn Tyr
            185                 190                 195

Ile Tyr Ala Ile Lys Pro Asp Ala Ile Asn Asn Glu Asn Ile Asn
            200                 205                 210

Ala Leu Thr Ala Thr Tyr His Gln Glu Asp Gly Phe Ile Tyr Ser
            215                 220                 225

Val Leu Ser Asp Val Asn Arg Val Gly Ser Glu Tyr Ile Pro Gln
            230                 235                 240

Tyr Gly Asn Val Ser Leu Thr Ile Gln Asn Gly Lys Ile Tyr Gly
            245                 250                 255

Glu Ile Tyr Arg His Asn Arg Gly Tyr Asp Asp Leu Phe Lys Leu
            260                 265                 270

Ser Gly Glu Gly Arg Asn Leu Ile Leu Thr Pro His Lys Asn Asn
            275                 280                 285

Pro Tyr Asp Leu Ser Pro Thr Gly Pro Asp Asn Met Thr Met Glu
            290                 295                 300

Leu Asn Phe Ile Asn Ala Glu Lys Thr Asp Lys Lys Tyr Val Val
            305                 310                 315

Gly Val Gly Lys Ala Glu Lys Tyr Tyr Gly Leu Leu Phe Ala Glu
            320                 325                 330

Lys Ser His Gln Ala Gln
            335

<210> SEQ ID NO 3
<211> LENGTH: 1008
<212> TYPE: DNA
<213> ORGANISM: P. multocida strain P-1059

<400> SEQUENCE: 3

```
atgaaacaaa tcgttttaaa aacaagctta ttgatgaccc tctcttcatt attagttgca      60
tgtagcggtg gtggcggtag cgctggaaat cgtgctgacc gtgtagagca aaaagcacaa     120
ccggttcaat caaatagtga gccttcttcc gctccaatca aaatcctac taataccgcc      180
acgaatgatt ctcttcatga caaactttca atgtcttccc atgacacatc caaagaaaat     240
agtcaacaat cctcctttca agcccctcta gaacaagaaa aaaccaacc tgcacaagaa      300
atcttacttt ggacaggtta tcatgtttca gaatggggaa atgcgagtaa taatgtagat     360
aaagataatg ttacggtatt cactttcgta aaatataatt ctcaatacaa tgatgatcca     420
gttttttgata aaacaaaaac acaagtaaaa acaatatcat tagttgacgg caaaaacgaa     480
agtaaagaag attattatca ctttacgcta aaagacgctt tattttatta tggcagttat     540
ggacaacctt cagcagatta caaaaaagta gaaaaaaatt atatttacgc gattaaacca     600
gatgcaataa ataatgagaa cctcaatgca ctaactgcaa cttaccatca agaagatggt     660
tttatatatt ccgtattaag tgatgtaaat cgagttggtt cagaatatat tgctcagtat     720
ggcaatgtga gtcttactat acaaaatggt aaaattcatg gtgagattta taggcataac     780
```

```
cgagggtacg atgatctatt taagctctct ggagaaggcc ggaatttaat attaacgcca    840
cataaaaata accctcatga cctttcccca acaggacccg acaacatgac aatggagctg    900
aattttatca acgcagaaaa gactgataaa aaatacgttg ttggtgtagg aaaagctgaa    960
aaatattatg ggttattatt tgctgaaaaa agtcaccaag cacaataa                1008
```

<210> SEQ ID NO 4
<211> LENGTH: 335
<212> TYPE: PRT
<213> ORGANISM: P. multocida strain P-1059

<400> SEQUENCE: 4

```
Met Lys Gln Ile Val Leu Lys Thr Ser Leu Leu Met Thr Leu Ser
1               5                   10                  15

Ser Leu Leu Val Ala Cys Ser Gly Gly Gly Ser Ala Gly Asn
                20                  25                  30

Arg Ala Asp Arg Val Glu Gln Lys Ala Gln Pro Val Gln Ser Asn
                35                  40                  45

Ser Glu Pro Ser Ser Ala Pro Ile Lys Asn Pro Thr Asn Thr Ala
                50                  55                  60

Thr Asn Asp Ser Leu His Asp Lys Leu Ser Met Ser Ser His Asp
                65                  70                  75

Thr Ser Lys Glu Asn Ser Gln Gln Ser Phe Gln Ala Pro Leu
                80                  85                  90

Glu Gln Glu Lys Asn Gln Pro Ala Gln Glu Asn Leu Thr Trp Thr
                95                  100                 105

Gly Tyr His Val Ser Glu Trp Gly Asn Ala Ser Asn Asn Val Asp
                110                 115                 120

Lys Asp Asn Val Thr Val Phe Thr Phe Val Lys Tyr Asn Ser Gln
                125                 130                 135

Tyr Asn Asp Asp Pro Val Phe Asp Lys Thr Lys Thr Gln Ser Lys
                140                 145                 150

Thr Ile Ser Leu Val Asp Gly Lys Asn Glu Ser Lys Glu Asp Tyr
                155                 160                 165

Tyr His Phe Thr Leu Lys Asp Ala Leu Phe Tyr Tyr Gly Ser Tyr
                170                 175                 180

Gly Gln Pro Ser Ala Asp Tyr Lys Lys Val Glu Lys Asn Tyr Ile
                185                 190                 195

Tyr Ala Ile Lys Pro Asp Ala Ile Asn Asn Glu Asn Leu Asn Ala
                200                 205                 210

Leu Thr Ala Thr Tyr His Gln Glu Asp Gly Phe Ile Tyr Ser Val
                215                 220                 225

Leu Ser Asp Val Asn Arg Val Gly Ser Glu Tyr Ile Ala Gln Tyr
                230                 235                 240

Gly Asn Val Ser Leu Thr Ile Gln Asn Gly Lys Ile His Gly Glu
                245                 250                 255

Ile Tyr Arg His Asn Arg Gly Tyr Asp Asp Leu Phe Lys Leu Ser
                260                 265                 270

Gly Glu Gly Arg Asn Leu Ile Leu Thr Pro His Lys Asn Asn Pro
                275                 280                 285

His Asp Leu Ser Pro Thr Gly Pro Asp Asn Met Thr Met Glu Leu
                290                 295                 300

Asn Phe Ile Asn Ala Glu Lys Thr Asp Lys Lys Tyr Val Val Gly
                305                 310                 315

Val Gly Lys Ala Glu Lys Tyr Tyr Gly Leu Leu Phe Ala Glu Lys
```

```
            320                 325                 330
Ser His Gln Ala Gln
                335

<210> SEQ ID NO 5
<211> LENGTH: 1008
<212> TYPE: DNA
<213> ORGANISM: P. multocida strain P-1662

<400> SEQUENCE: 5
atgaaacaaa tcgttttaaa aacaagctta ttgatgaccc tctcttcatt attagttgca      60
tgtagcggtg gtggcggtag cgctggaaat cgtgctgacc gtgtagagca aaaagcacaa     120
ccggttcaat caaatagtga gccttcttcc gctccaatca aaaatcctac taataccgcc     180
acgaatgatt ctcttcatga caaactttca atgtcttctc atgacacatc aaagaaaat      240 agtcaacaat cctcctttca agcccctcta gaacaagaaa aaaacaacc tgcacaagaa      300 aatcttactt ggacaggtta tcatgtttca gaagtgggaa atgcgagtaa taatgtagat     360
aaagataatg ttacggtatt cactttcgta gaatataatt ctcaatacaa tgatgatcca     420
gtttttgata aaacaaaaac acaagtaaaa acaatatcat tagttgacgg caaaaacgaa     480
agtaaagaag attattatca ctttacgcta aaagacgctt tattttatta tggcagttat     540
ggacaacctt cagcagatta caaaaaagta gaaaaaaatt atatttacgc gattaaacca     600
gatgcaataa ataatgagaa cctcaatgca ctaactgcaa cttaccatca agaagatggt     660
tttatatatt ccgtattaag tgatgtaaat cgagttggtt cagaatatat tcctcagtat     720
ggcaatgtga ctcttacttt ccgaaatggc aagatttatg gtgaaatcta cagatataat     780
agaggacgtg atgatttgtt tcagctctct ggagaagacc ggaatttaat attaacgcca     840
cataaaaata accctcatga tctttcccca acaggacccg acaacatgac aatggagctg     900
aattttatca acgcagaaaa gactgataaa aaatacgttg ttggtgtagg aaaagctgaa     960
aaatattatg ggttattatt tgctgaaaaa agtcaccaag cacaataa                 1008

<210> SEQ ID NO 6
<211> LENGTH: 335
<212> TYPE: PRT
<213> ORGANISM: P. multocida strain P-1662

<400> SEQUENCE: 6

Met Lys Gln Ile Val Leu Lys Thr Ser Leu Leu Met Thr Leu Ser
1               5                   10                  15

Ser Leu Leu Val Ala Cys Ser Gly Gly Gly Gly Ser Ala Gly Asn
            20                  25                  30

Arg Ala Asp Arg Val Glu Gln Lys Ala Gln Pro Val Gln Ser Asn
            35                  40                  45

Ser Glu Pro Ser Ala Pro Ile Lys Asn Pro Thr Asn Thr Ala
            50                  55                  60

Thr Asn Asp Ser Leu His Asp Lys Leu Ser Met Ser Ser His Asp
            65                  70                  75

Thr Ser Lys Glu Asn Ser Gln Gln Ser Ser Phe Gln Ala Pro Leu
            80                  85                  90

Glu Gln Glu Lys Lys Gln Pro Ala Gln Glu Asn Leu Thr Trp Thr
            95                  100                 105

Gly Tyr His Val Ser Glu Val Gly Asn Ala Ser Asn Asn Val Asp
            110                 115                 120

Lys Asp Asn Val Thr Val Phe Thr Phe Val Glu Tyr Asn Ser Gln
```

```
                125                 130                 135
Tyr Asn Asp Asp Pro Val Phe Asp Lys Thr Lys Thr Gln Ser Lys
            140                 145                 150

Thr Ile Ser Leu Val Asp Gly Lys Asn Glu Ser Lys Glu Asp Tyr
            155                 160                 165

Tyr His Phe Thr Leu Lys Asp Ala Leu Phe Tyr Tyr Gly Ser Tyr
            170                 175                 180

Gly Gln Pro Ser Ala Asp Tyr Lys Lys Val Glu Lys Asn Tyr Ile
            185                 190                 195

Tyr Ala Ile Lys Pro Asp Ala Ile Asn Asn Glu Asn Leu Asn Ala
            200                 205                 210

Leu Thr Ala Thr Tyr His Gln Glu Asp Gly Phe Ile Tyr Ser Val
            215                 220                 225

Leu Ser Asp Val Asn Arg Val Gly Ser Glu Tyr Ile Pro Gln Tyr
            230                 235                 240

Gly Asn Val Thr Leu Thr Phe Arg Asn Gly Lys Ile Tyr Gly Glu
            245                 250                 255

Ile Tyr Arg Tyr Asn Arg Gly Arg Asp Asp Leu Phe Gln Leu Ser
            260                 265                 270

Gly Glu Asp Arg Asn Leu Ile Leu Thr Pro His Lys Asn Asn Pro
            275                 280                 285

His Asp Leu Ser Pro Thr Gly Pro Asp Asn Met Thr Met Glu Leu
            290                 295                 300

Asn Phe Ile Asn Ala Glu Lys Thr Asp Lys Lys Tyr Val Val Gly
            305                 310                 315

Val Gly Lys Ala Glu Lys Tyr Tyr Gly Leu Leu Phe Ala Glu Lys
            320                 325                 330

Ser His Gln Ala Gln
            335

<210> SEQ ID NO 7
<211> LENGTH: 1008
<212> TYPE: DNA
<213> ORGANISM: P. multocida strain P-470

<400> SEQUENCE: 7
atgaaacaaa tcgttttaaa aacaagctta ttgatgaccc tctcttcatt attagttgca    60
tgtagcggtg gtggcggtag cgctggaaat cgtgctgacc gtgtagagca aaaagcacaa   120
ccggttcaat caaatagtga gccttcttcc gctccaatca aaatcctac taataccgcc    180 acgaatgatt ctcttcatga cagactttca atgtcttctc atgacacatc caagaaaat   240 agtcaacaat cctcctttca gcccctctca gaacaagaaa aaaaccaacc tgcacaagaa   300 atcttactt ggacaggtta tcatgtttca gaatggggaa atgcgagtaa taatgtagat    360
aaagataatg ttacggtatt cactttcgta aaatataatt ctcaatacaa tgatgatcca   420 gttttgata aacaaaaac acaaagtaaa acaatatcat tagttgacgg caaaaacgaa    480
agtaaagaag attattatca ctttacgcta aagacgcctt tatttttatta tggcagttat   540 ggacaacctt cagcagatta caaaaaagta gaaaaaaatt atatttacgc gattaaacca   600
gatgcaataa ataatgagaa cctcaatgca ctaactgcaa cttaccatca agaagatggt   660
tttatatatt ccgtattaag tgatgtaaat cgagttggtt cagaatatat tgctcagtat   720
ggcaatgtga gtcttactat acaaaatggt aaaattcatg gtgagattta taggcataac   780
cgagggtacg atgatctatt taagctctct ggagaaggcc ggaatttaat attaacgcca   840
```

```
cataaaaata accctcatga tctttcccca acaggacccg acaacatgac aatggagctg    900
aattttatca acgcagaaaa gactgataaa aaatacgttg ttggtgtagg aaaagctgaa    960
aaatattatg ggttattatt tgctgaaaaa agtcaccaag cacaataa                1008
```

<210> SEQ ID NO 8
<211> LENGTH: 335
<212> TYPE: PRT
<213> ORGANISM: P. multocida strain P-470

<400> SEQUENCE: 8

```
Met Lys Gln Ile Val Leu Lys Thr Ser Leu Leu Met Thr Leu Ser
 1               5                  10                  15

Ser Leu Leu Val Ala Cys Ser Gly Gly Gly Gly Ser Ala Gly Asn
                20                  25                  30

Arg Ala Asp Arg Val Glu Gln Lys Ala Gln Pro Val Gln Ser Asn
                35                  40                  45

Ser Glu Pro Ser Ser Ala Pro Ile Lys Asn Pro Thr Asn Thr Ala
                50                  55                  60

Thr Asn Asp Ser Leu His Asp Arg Leu Ser Met Ser Ser His Asp
                65                  70                  75

Thr Ser Lys Glu Asn Ser Gln Gln Ser Ser Phe Gln Ala Pro Leu
                80                  85                  90

Glu Gln Glu Lys Asn Gln Pro Ala Gln Glu Asn Leu Thr Trp Thr
                95                  100                 105

Gly Tyr His Val Ser Glu Trp Gly Asn Ala Ser Asn Asn Val Asp
                110                 115                 120

Lys Asp Asn Val Thr Val Phe Thr Phe Val Lys Tyr Asn Ser Gln
                125                 130                 135

Tyr Asn Asp Asp Pro Val Phe Asp Lys Thr Lys Thr Gln Ser Lys
                140                 145                 150

Thr Ile Ser Leu Val Asp Gly Lys Asn Glu Ser Lys Glu Asp Tyr
                155                 160                 165

Tyr His Phe Thr Leu Lys Asp Ala Leu Phe Tyr Tyr Gly Ser Tyr
                170                 175                 180

Gly Gln Pro Ser Ala Asp Tyr Lys Lys Val Glu Lys Asn Tyr Ile
                185                 190                 195

Tyr Ala Ile Lys Pro Asp Ala Ile Asn Asn Glu Asn Leu Asn Ala
                200                 205                 210

Leu Thr Ala Thr Tyr His Gln Glu Asp Gly Phe Ile Tyr Ser Val
                215                 220                 225

Leu Ser Asp Val Asn Arg Val Gly Ser Glu Tyr Ile Ala Gln Tyr
                230                 235                 240

Gly Asn Val Ser Leu Thr Ile Gln Asn Gly Lys Ile His Gly Glu
                245                 250                 255

Ile Tyr Arg His Asn Arg Gly Tyr Asp Asp Leu Phe Lys Leu Ser
                260                 265                 270

Gly Glu Gly Arg Asn Leu Ile Leu Thr Pro His Lys Asn Asn Pro
                275                 280                 285

His Asp Leu Ser Pro Thr Gly Pro Asp Asn Met Thr Met Glu Leu
                290                 295                 300

Asn Phe Ile Asn Ala Glu Lys Thr Asp Lys Lys Tyr Val Val Gly
                305                 310                 315

Val Gly Lys Ala Glu Lys Tyr Tyr Gly Leu Leu Phe Ala Glu Lys
                320                 325                 330
```

Ser His Gln Ala Gln
            335

<210> SEQ ID NO 9
<211> LENGTH: 1008
<212> TYPE: DNA
<213> ORGANISM: P. multocida strain P-61

<400> SEQUENCE: 9

```
atgaaacaaa tcgttttaaa aacaagctta ttgatgaccc tctcttcatt attagttgca      60
tgtagcggtg gtggcggtag cgctggaaat cgtgctgacc gtgtagagca aaaagcacaa     120
ccggttcaat caaatagtga gccttcttcc gctccaatca aaaatcctac taataccgcc     180
acgaatgatt ctcttcatga caaactttca atgtcttctc atgacacatc aaagagaat     240
agtcaacaat cctcctttca agcccctcta gaacaagaaa aaaccaacc tgcacaagaa      300
aatcttactt ggacaggtta tcatgtttca gaatggggaa atgcgagtaa taatgtagat     360
aaagataatg ttacggtatt cactttcgta aaatataatt ctcaatacaa tgatgatcca     420
gttttttgata aacaaaaac acaaagtaaa acaatatcat tagttgacgg caaaaacgaa     480
agtaaagaag attattatca ctttacgcta aaagacgctt tatttattta tggcagttat     540
ggacaacctt cagcagatta caaaaaagta gaaaaaaatt atatttacgc gattaaacca     600
gatgcaataa ataatgagaa cctcaatgca ctaactgcaa cttaccatca agaagatggt     660
tttatatatt ccgtattaag tgatgtaaat cgagttggtt cagaatatat tgctcagtat     720
ggcaatgtga gtcttactat acaaaatggt aaaattcatg gtgagattta taggcataac     780
cgagggtacg atgatctatt taagctctct ggagaaggcc ggaatttaat attaacgcca     840
cataaaaata accctcatga tctttcccca acaggacccg acaacatgac aatggagctg     900
aattttatca acgcagaaaa gactgataaa aaatacgttg ttggtgtagg aaaagctgaa     960
aaatattatg ggttattatt tgctgaaaaa agtcaccaag cacaataa                 1008
```

<210> SEQ ID NO 10
<211> LENGTH: 335
<212> TYPE: PRT
<213> ORGANISM: P. multocida strain P-61

<400> SEQUENCE: 10

Met Lys Gln Ile Val Leu Lys Thr Ser Leu Leu Met Thr Leu Ser
1               5                   10                  15

Ser Leu Leu Val Ala Cys Ser Gly Gly Gly Gly Ser Ala Gly Asn
                20                  25                  30

Arg Ala Asp Arg Val Glu Gln Lys Ala Gln Pro Val Gln Ser Asn
                35                  40                  45

Ser Glu Pro Ser Ser Ala Pro Ile Lys Asn Pro Thr Asn Thr Ala
                50                  55                  60

Thr Asn Asp Ser Leu His Asp Lys Leu Ser Met Ser Ser His Asp
                65                  70                  75

Thr Ser Lys Glu Asn Ser Gln Gln Ser Ser Phe Gln Ala Pro Leu
                80                  85                  90

Glu Gln Glu Lys Asn Gln Pro Ala Gln Glu Asn Leu Thr Trp Thr
                95                  100                 105

Gly Tyr His Val Ser Glu Trp Gly Asn Ala Ser Asn Asn Val Asp
                110                 115                 120

Lys Asp Asn Val Thr Val Phe Thr Phe Val Lys Tyr Asn Ser Gln
                125                 130                 135

```
Tyr Asn Asp Asp Pro Val Phe Asp Lys Thr Lys Thr Gln Ser Lys
                140                 145                 150

Thr Ile Ser Leu Val Asp Gly Lys Asn Glu Ser Lys Glu Asp Tyr
            155                 160                 165

Tyr His Phe Thr Leu Lys Asp Ala Leu Phe Tyr Tyr Gly Ser Tyr
        170                 175                 180

Gly Gln Pro Ser Ala Asp Tyr Lys Lys Val Glu Lys Asn Tyr Ile
    185                 190                 195

Tyr Ala Ile Lys Pro Asp Ala Ile Asn Asn Glu Asn Leu Asn Ala
200                 205                 210

Leu Thr Ala Thr Tyr His Gln Glu Asp Gly Phe Ile Tyr Ser Val
                215                 220                 225

Leu Ser Asp Val Asn Arg Val Gly Ser Glu Tyr Ile Ala Gln Tyr
            230                 235                 240

Gly Asn Val Ser Leu Thr Ile Gln Asn Gly Lys Ile His Gly Glu
        245                 250                 255

Ile Tyr Arg His Asn Arg Gly Tyr Asp Asp Leu Phe Lys Leu Ser
    260                 265                 270

Gly Glu Gly Arg Asn Leu Ile Leu Thr Pro His Lys Asn Asn Pro
275                 280                 285

His Asp Leu Ser Pro Thr Gly Pro Asp Asn Met Thr Met Glu Leu
                290                 295                 300

Asn Phe Ile Asn Ala Glu Lys Thr Asp Lys Lys Tyr Val Val Gly
            305                 310                 315

Val Gly Lys Ala Glu Lys Tyr Tyr Gly Leu Leu Phe Ala Glu Lys
        320                 325                 330

Ser His Gln Ala Gln
            335

<210> SEQ ID NO 11
<211> LENGTH: 1017
<212> TYPE: DNA
<213> ORGANISM: P. multocida strain 12948

<400> SEQUENCE: 11
atgaaacaaa tcgttttaaa aacaagctta ttgatgaccc tctcttcatt attagttgca      60
tgtagtggtg gtggcagtag tggtagcact ggaaatcgtg ctgaccgtgt agaagaaaaa     120
gcacaaccag ttcaattaaa tagtgagcct tcttccactc caatcaaaca tcctatgact     180
aatagtgcta cgagtacttc tcttcatgac aaactttcaa tgtcttctca tgacacatcc     240
aaagaaaata gtcaacaatc ctcctttcaa acctctctag aacaagaaaa aaaccaacct     300
gcacaagaaa tcttacttg acaggttat catgtttcag aatggggaaa tgcgagtaat     360
aatgtagata agataatgt tacggtattc actttcgtaa aatataattc tcaatataat     420
gatgatccag ttttttgataa aataaaaaca caaagtaaaa cgatatcatt agttgacgga     480
aaaaatgaaa ataaagagca ttattatcac tttacgttaa aagacgcttt attttattat     540
ggaagttatg gacaaccttc agcagattac aaaaaggtag aagaaaatta tatttatgcg     600
attaaaccag atgcaataaa taatgagaac ctcaatgcac taactgcaac ttattatcaa     660
gaagatggtt ttatatattc cgtattaagt gatgtaaatc gagttggttc agaatatatt     720
cctcagtatg gcaatgtgag tcttactata caaaatggta aaattcatgg tgagatttac     780
aagtataacc gagggtatga tgatctattt aagctctctg gagaaggtcg gaatttaata     840
ttaacgccac ataaaaataa ccccccatgct ctttcttcta gaggacccga caatatggta     900
```

```
atggagctga attttatcaa cgcagaaaaa actgataaaa aatacgttgt tggtgtagga        960
aaagctgaaa atattatgg gttattattt gctgaaaaaa gtcaccaagc acaataa          1017
```

<210> SEQ ID NO 12
<211> LENGTH: 338
<212> TYPE: PRT
<213> ORGANISM: P. multocida strain 12948

<400> SEQUENCE: 12

```
Met Lys Gln Ile Val Leu Lys Thr Ser Leu Leu Met Thr Leu Ser
1               5                   10                  15

Ser Leu Leu Val Ala Cys Ser Gly Gly Gly Ser Ser Gly Ser Thr
                20                  25                  30

Gly Asn Arg Ala Asp Arg Val Glu Glu Lys Ala Gln Pro Val Gln
                35                  40                  45

Leu Asn Ser Glu Pro Ser Ser Thr Pro Ile Lys His Pro Met Thr
                50                  55                  60

Asn Ser Ala Thr Ser Thr Ser Leu His Asp Lys Leu Ser Met Ser
                65                  70                  75

Ser His Asp Thr Ser Lys Glu Asn Ser Gln Gln Ser Ser Phe Gln
                80                  85                  90

Thr Ser Leu Glu Gln Glu Lys Asn Gln Pro Ala Gln Glu Asn Leu
                95                  100                 105

Thr Trp Thr Gly Tyr His Val Ser Glu Trp Gly Asn Ala Ser Asn
                110                 115                 120

Asn Val Asp Lys Asp Asn Val Thr Val Phe Thr Phe Val Lys Tyr
                125                 130                 135

Asn Ser Gln Tyr Asn Asp Asp Pro Val Phe Asp Lys Ile Lys Thr
                140                 145                 150

Gln Ser Lys Thr Ile Ser Leu Val Asp Gly Lys Asn Glu Asn Lys
                155                 160                 165

Glu His Tyr Tyr His Phe Thr Leu Lys Asp Ala Leu Phe Tyr Tyr
                170                 175                 180

Gly Ser Tyr Gly Gln Pro Ser Ala Asp Tyr Lys Lys Val Glu Glu
                185                 190                 195

Asn Tyr Ile Tyr Ala Ile Lys Pro Asp Ala Ile Asn Asn Glu Asn
                200                 205                 210

Leu Asn Ala Leu Thr Ala Thr Tyr Tyr Gln Glu Asp Gly Phe Ile
                215                 220                 225

Tyr Ser Val Leu Ser Asp Val Asn Arg Val Gly Ser Glu Tyr Ile
                230                 235                 240

Pro Gln Tyr Gly Asn Val Ser Leu Thr Ile Gln Asn Gly Lys Ile
                245                 250                 255

His Gly Glu Ile Tyr Lys Tyr Asn Arg Gly Tyr Asp Asp Leu Phe
                260                 265                 270

Lys Leu Ser Gly Glu Gly Arg Asn Leu Ile Leu Thr Pro His Lys
                275                 280                 285

Asn Asn Pro His Ala Leu Ser Ser Arg Gly Pro Asp Asn Met Val
                290                 295                 300

Met Glu Leu Asn Phe Ile Asn Ala Glu Lys Thr Asp Lys Lys Tyr
                305                 310                 315

Val Val Gly Val Gly Lys Ala Glu Lys Tyr Tyr Gly Leu Leu Phe
                320                 325                 330

Ala Glu Lys Ser His Gln Ala Gln
                335
```

```
<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13 atg aaa caa atc gtt tta aa                                              20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14 tta ttg tgc ttg gtg act tt                                              20
```